(12) United States Patent
Hochrainer et al.

(10) Patent No.: US 8,298,575 B2
(45) Date of Patent: Oct. 30, 2012

(54) TWO-PART CAPSULE TO ACCEPT PHARMACEUTICAL PREPARATIONS FOR POWDER INHALERS

(75) Inventors: Dieter Hochrainer, Bingen am Rhein (DE); Josef Eckert, Mellrichstadt (DE)

(73) Assignee: Boehringer Ingelheim Pharma GmbH & Co. KG, Ingelheim am Rhein (DE)

( * ) Notice: Subject to any disclaimer, the term of this patent is extended or adjusted under 35 U.S.C. 154(b) by 0 days.

(21) Appl. No.: 11/970,982

(22) Filed: Jan. 8, 2008

(65) Prior Publication Data

US 2008/0160076 A1 Jul. 3, 2008

Related U.S. Application Data

(63) Continuation of application No. 10/740,225, filed on Dec. 18, 2003, now abandoned, which is a continuation of application No. 09/800,647, filed on Mar. 7, 2001, now abandoned, which is a continuation of application No. 09/365,912, filed on Aug. 3, 1999, now abandoned.

(60) Provisional application No. 60/113,214, filed on Dec. 22, 1998.

(30) Foreign Application Priority Data

Aug. 5, 1998 (DE) .................................. 198 35 346

(51) Int. Cl.
*A61K 9/48* (2006.01)
*A61K 31/439* (2006.01)
(52) U.S. Cl. ........................................ 424/454; 424/453
(58) Field of Classification Search .................. 424/454, 424/453
See application file for complete search history.

(56) References Cited

U.S. PATENT DOCUMENTS

| 596,591 | A | 1/1898 | Higgins |
| 2,718,980 | A | 9/1955 | Strom |
| 3,159,545 | A | 12/1964 | Kidwell |
| 3,285,408 | A | 11/1966 | Carnaghi |

(Continued)

FOREIGN PATENT DOCUMENTS

CA   2338323 A1   2/2000

(Continued)

OTHER PUBLICATIONS

Slepian (β3-Integrins Rather than β1-Integrins Dominate Interfin-Matrix Interactions Involved in Postingury Smooth Muscle Cell Migration, American Heart Association, May 12, 1998; 97: pp. 1818-1827).*

(Continued)

*Primary Examiner* — San-Ming Hui
*Assistant Examiner* — Kathrien Cruz
(74) *Attorney, Agent, or Firm* — Michael P. Morris; Wendy A. Petka

(57) ABSTRACT

The present invention relates to capsules for holding pharmaceutical preparations for powder inhalers with increased drug safety and capsules for pharmaceutical preparations for powder inhalers with improved adaptation to their use in powder inhalers. The capsules consist of water-insoluble hydrophobic synthetic materials which do not significantly affect the pharmaceutical quality of the contents themselves, but which improve the usability of the filled capsules with regard to their function, their longevity, and/or the geographic location of their use, and are advantageous at various stages from manufacture up to utilization.

11 Claims, 4 Drawing Sheets

U.S. PATENT DOCUMENTS

| | | |
|---|---|---|
| 3,623,997 A | 11/1971 | Powell |
| 3,664,495 A | 5/1972 | Graham |
| 3,807,400 A | 4/1974 | Cocozza |
| 3,823,843 A | 7/1974 | Stephens |
| 3,949,751 A | 4/1976 | Birch |
| 3,991,761 A | 11/1976 | Cocozza |
| 4,040,536 A | 8/1977 | Schwarz |
| 4,069,819 A | 1/1978 | Valentini |
| 4,192,309 A | 3/1980 | Paulsen |
| 4,196,565 A | 4/1980 | Bodenmann |
| 4,210,140 A | 7/1980 | Hallworth |
| 4,353,365 A | 10/1982 | Hallworth |
| 4,489,327 A | 12/1984 | Eastwell |
| 4,533,542 A | 8/1985 | Buddenbaum et al. |
| 4,535,567 A | 8/1985 | Seaborn |
| 4,648,532 A | 3/1987 | Green |
| 4,656,066 A | 4/1987 | Wittwer |
| 4,667,498 A | 5/1987 | Sauter |
| 4,692,314 A | 9/1987 | Etani |
| 4,738,724 A | 4/1988 | Wittwer et al. |
| 4,792,451 A | 12/1988 | Kim |
| 4,793,493 A | 12/1988 | Makiej, Jr. |
| 4,860,740 A | 8/1989 | Kirk |
| 4,863,017 A | 9/1989 | Vlock |
| 4,880,547 A | 11/1989 | Etani |
| 4,883,182 A | 11/1989 | Hughes |
| 4,889,114 A | 12/1989 | Kladders |
| 4,892,766 A | 1/1990 | Jones |
| 4,893,721 A * | 1/1990 | Bodenmann et al. ............ 220/8 |
| 5,152,284 A | 10/1992 | Valentini |
| 5,223,265 A | 6/1993 | Wong |
| 5,283,064 A | 2/1994 | Suzuki |
| 5,342,624 A | 8/1994 | McNeil et al. |
| 5,370,879 A | 12/1994 | Masterson et al. |
| 5,388,698 A | 2/1995 | Wakao |
| 5,396,986 A | 3/1995 | Fountain et al. |
| 5,498,255 A | 3/1996 | Wong |
| 5,575,398 A | 11/1996 | Robbins, III |
| 5,587,177 A | 12/1996 | Grimberg |
| 5,632,971 A | 5/1997 | Yang |
| 5,641,510 A | 6/1997 | Clark |
| 5,673,686 A | 10/1997 | Villax |
| 5,685,294 A | 11/1997 | Gupte |
| 5,750,143 A | 5/1998 | Rashid |
| 5,752,505 A | 5/1998 | Ohki |
| 5,770,224 A | 6/1998 | Rashid et al. |
| 5,795,591 A | 8/1998 | Lee et al. |
| 5,881,721 A | 3/1999 | Bunce |
| 5,947,118 A | 9/1999 | Hochrainer |
| 6,488,027 B1 | 12/2002 | Moulin |
| 6,762,005 B2 | 7/2004 | Katano et al. |
| 6,941,954 B1 | 9/2005 | Belcher |
| 6,941,980 B2 | 9/2005 | Rocchio et al. |
| 6,949,154 B2 | 9/2005 | Hochrainer et al. |
| 7,252,087 B2 | 8/2007 | Wachtel |
| 7,284,553 B2 | 10/2007 | Hochrainer |
| 2001/0008637 A1 | 7/2001 | Hochrainer |
| 2003/0106827 A1 | 6/2003 | Cheu et al. |
| 2003/0183548 A1 | 10/2003 | Oertel |
| 2004/0025876 A1 | 2/2004 | Miller et al. |
| 2004/0131668 A1 | 7/2004 | Hochrainer |

FOREIGN PATENT DOCUMENTS

| | | |
|---|---|---|
| DE | 1516488 A1 | 1/1970 |
| DE | 33 45 722 A1 | 6/1985 |
| DE | 4318455 A1 | 12/1994 |
| EP | 0110500 A1 | 6/1984 |
| EP | 0 143 524 | 6/1985 |
| EP | 0 147 755 A2 | 7/1985 |
| EP | 0460921 A2 | 12/1991 |
| EP | 0597136 A1 | 5/1994 |
| EP | 1100474 A2 | 5/2001 |
| FR | 2 380 032 A1 | 9/1978 |
| GB | 691696 A | 5/1953 |
| GB | 938828 A | 10/1963 |
| GB | 2 064 336 A | 6/1981 |
| JP | 5352619 A | 5/1978 |
| JP | 5271055 A | 10/1993 |
| JP | 7118143 A | 5/1995 |
| JP | 3028641 U | 9/1996 |
| JP | 8229101 A | 9/1996 |
| JP | 9104060 A | 4/1997 |
| JP | 9193963 A | 7/1997 |
| JP | 10-502283 A | 3/1998 |
| WO | 82 01470 A1 | 5/1982 |
| WO | 9428958 A1 | 12/1994 |
| WO | 9601105 A1 | 1/1996 |

OTHER PUBLICATIONS

Brandrup, J. & Immergut, E.H., Polymer Handbook, pp. 436-437, copyright 1989, Third Edition, John Wiley & Sons, U.S.

M. Matumoto et al., ed. Pharmaceutics Manual, 1st. Edition Nanzando p. 123, 1989 (See translation of relevant part provided).

Okano ed. New General Pharmaceutics, revised 3rd edition Nanzando p. 367, 1987 (See translation of relevant part provided).

Ansel, H. C. Introduchtion to Pharmaceutical Dosage Forms, 4th Ed., 1985 Lea & Febiger, Philadelphia, pp. 128-131.

Kirk-Othmer Encyclopedia of Chemical Technology, Ed. M. Howe-Grant, 1996. p. 729.

* cited by examiner

TWO-PART CAPSULE TO ACCEPT PHARMACEUTICAL PREPARATIONS FOR POWDER INHALERS

The invention relates to new two-part capsules for holding pharmaceutical preparations for use in powder inhalers.

THE PRIOR ART

Capsules with pharmaceutical preparations are often used in the therapy and diagnosis of illnesses. The capsules can be orally administered or are used in certain medical apparatus such as powder inhalers. Generally, the capsules consist of two parts, a capsule body (body) and a capsule cap (cap), which are pushed together telescopically. However, multi-part capsules are also known. The capsules generally consist of gelatin, especially hard gelatin. In the case of some special applications, the capsules occasionally consist of water-soluble synthetic materials easily digested by humans, in order for example to release the active ingredients in certain compartments of the gastrointestinal tract in the case of oral administration. Examples of various capsule materials are listed hereinafter.

EP 0143524 discloses a two-part capsule of material which is easily digestible by humans, preferably gelatin.

EP 0460921 describes capsules of chitosan and starch, grain powder, oligosaccharides, methacrylic acid-methylacrylate, methacrylic acid-ethylacrylate, hydroxypropylmethylcelluloseacetate, succinate, or phthaleate. The capsule material is distinguished by the contents not being released until they reach the large intestine.

GB 938828 discloses capsules for radioactive substances used in therapy or diagnosis. The capsules comprise water-soluble gelatin, methylcellulose, polyvinylalcohol or water-soluble non-toxic thermoplasts.

The materials which are used are often not very resistant to air humidity, which is why the pharmaceutical quality of the contents cannot be guaranteed for all climatic zones. Especially in climatic zone 4 (30° C./70% relative air humidity), conventional capsules cannot be used.

Two-part capsules, which are specially adapted for use in powder inhalers without necessarily being subjected to the conditions for oral administration, are previously not known in the prior art. The capsules for powder inhalers comprise the same materials as are used for oral administration, usually hard gelatin. However, these materials are not specially perfected for use in powder inhalers.

One of the objectives of the present invention is to provide capsules which can be better adapted to the special conditions in powder inhalers.

The capsules which have hitherto been used in powder inhalers have various disadvantages as a result of their composition. Hence, materials used in construction of the capsules can alter their characteristics dependent on the ambient air humidity and/or do not always have sufficient inherent stability. As a result, such a capsule cannot for example be used in climatic zone 4 as a result of the high air humidity, since the capsule material absorbs the humidity to such a degree that the inherent stability is seriously affected and/or the humidity penetrates into the interior of the capsule. This has a negative effect on the pharmaceutical quality of the capsule's contents. The said materials also have diverse disadvantages in other various stages in the life of the capsule from manufacturing up to utilisation, which affect the suitability of the capsule as a carrier for pharmaceutical preparations, the manner of administration of the contents, the perishability of the contents and/or the usability of the capsule in certain countries. A further disadvantage of conventional capsule materials is that e.g. they tend to bind powder materials to themselves, especially when coated with a mould release agent which is often necessary for production of the capsule. In the case of capsules for inhalation purposes, this leads to difficulty in accurately metering the fine fraction which is to enter the lungs.

A further objective of the present invention is to provide capsules for powder inhalers which do not have the aforementioned problems of conventional capsules.

DESCRIPTION OF THE INVENTION

The present invention relates to a capsule for holding pharmaceutical preparations for powder inhalers with increased drug safety and capsules for pharmaceutical preparations for powder inhalers with improved adaptation to use in powder inhalers. The capsules consist of water-insoluble, hydrophobic synthetic materials, which do not themselves substantially influence the pharmaceutical quality of the contents, but which improve the usability of the filled capsules with regard to their function, their longevity and/or the climatic zone, and are advantageous at various stages from production through to utilization.

The capsules, according to the invention, consist of two parts, a capsule body (body) and a capsule cap (cap), which can be connected together so as to form a stable enclosed hollow space of defined volume which contains the pharmaceutical formulation. The dimensions of the capsule are chosen so that the capsule can be used with common powder inhalers which are used with capsules, such as those described for example in patent documents DE 33 45 722 (Inhaler Ingelheim M), EP 0 591 136 (Inhaler Ingelheim) or in the published German application DE 43 18 455 ("Handi-Haler®").

DETAILED DESCRIPTION OF THE INVENTION

In one embodiment, the synthetic material of the capsule is not digestible by humans, so that the active ingredient is not released when the capsule is taken orally. This has the advantage that inadvertent swallowing of the capsule cannot lead to a detrimental effect on health. This applies especially to small children or older people.

Preferably, synthetic materials are used which can be processed using injection molding or blow casting and/or synthetic materials where no mould release agent is necessary for their processing into capsule caps or capsule bodies, which can cause adhesion of the contents to the capsule wall. This has the advantage that the interior of the cap or the body need not be cleaned from mould separation agent, in order for example to meet the official requirements (e.g., according to DAB (Deutsches Apotheker Buch)), which restricts the use of mould release agents for primary packaging means.

In a preferred embodiment of the invention, the synthetic material does not exhibit any pronounced adhesion for pharmaceutical-chemical materials, especially for particles of lung-accessible size, so that when the capsule is used in one of the aforementioned inhalers, the entire contents of the capsule can be released. This has the advantage that exact dosage, especially of the lung-accessible fine fraction, is possible.

In a further embodiment, the capsule consists of a synthetic material with a Shore hardness D of 65 to 73. A synthetic material of this hardness does not shatter when it is pierced or cut open, but at the same time it is rigid enough so that the resulting hole does not close up again. The advantage of such material is that no fragments can be forced out of the capsule during opening, piercing, or slicing open of the capsule in the powder inhaler which can be breathed in during inhalation.

In one embodiment, the synthetic material capsule is so stable that it can withstand a force along its longitudinal axis or transverse axis of up to 15 N. The advantage of this is that the capsule is better adapted to the stress which acts upon it during manufacture, filling, packaging, transportation, and the like.

In a further embodiment, the wall of the capsule has a steam permeability of less than $1.3 \times 10^{-14}$ kg/(m² s Pa), preferably of $1.5 \times 10^{-16}$ to $2 \times 10^{-16}$ kg/(m² s Pa). The advantage of this feature is that the contents of the capsule are also protected from water in geographical zones with high air humidity.

In preferred embodiments, the synthetic material is polyethylene, especially polyethylene with a density of between 9000 and 10,000 kg/m³, preferably 9600 kg/m³ (high-density polyethylene), polycarbonate, polyester, polypropylene, or polyethyleneterephthalate.

In a preferred embodiment, the cap and the body have the shape of a cylinder with a round cross-section and a convex, practically hemispherical closed underside, and both consist of high-density polyethylene with a density of between 9500 and 10000 kg/m³.

The capsules according to the invention can be used in all kinds of powder inhalers where the preparation which is to be inhaled is administered by means of a capsule.

In a preferred embodiment, the cap and body of the capsule are of mutually-similar cylindrical shape, comprising an inherently closed jacket with, in each case, a closed end and an open end. Here, the shape and size of the cap and the capsule are such that the body can be pushed telescopically into the open end of the cap with its open end, so that the cap is attached solidly to the body.

In a special embodiment, the cap and body are provided with locking devices, which are advantageous for temporary and/or final closure of the capsule.

In such an embodiment, there are point-shaped elevations on the inner jacket of the cap and on the outer jacket of the body there are somewhat larger point-shaped recesses which are arranged so that the elevations engage with the recesses on closure of the capsule. Alternatively, the elevations can be located on the outer jacket of the body and the recesses on the inner jacket of the cap. Arrangements are preferred where the elevations or recesses are respectively disposed in a ring or spiral shape about the jacket. Instead of the point-shaped design of the elevations and recesses, these can also run continuously around the cap or the body in a ring-shape.

In one embodiment, one or more elevations, running annularly around the inner jacket of the cap and the outer jacket of the body, are designed so that elevations on the cap are each positioned next to an elevation of the body when the capsule is closed.

In embodiments with the aforementioned annular recesses and/or elevations, these can be continuous or interrupted.

In a further embodiment, elevations are formed on the outside of the body near the open end and holes are formed in the cap near the open end so that the elevations of the body locate into the holes in the cap when the capsule is closed. The elevations can be designed so that the cap can be opened at any time without damage to the capsule, or so that once closed, the capsule can no longer be opened without being damaged.

In a further embodiment, a bulge is designed on the outer side of the body, which runs around the body perpendicular to the connecting axis between the cap and the body. The bulge serves as a stopper for the capsule when this is placed over the body, in order to prevent piercing of the cap with the body.

The area between the open end of the body and the bulge corresponds to the area of the body over which the cap can be pushed. The bulge is located on the body so that the cap can be pushed far enough over the body to ensure good attachment between the cap and the body. That is, the bulge may not, for example, be located directly on the open side of the body. The side of the bulge which faces the open end of the body stands as a vertical edge on the outer wall of the body so that the cap cannot be pushed over the bulge on closure. The side of the bulge which faces towards the closed end of the body can be designed in the form of an almost right-angled edge or can taper towards the closed end of the body. The formation of a practically right-angled edge can be advantageous where the capsule fits loosely into the capsule holder, whilst the version with the tapering bulge can be advantageous in the case of a tight fit. The bulge can be continuous or interrupted.

In a preferred embodiment, the bulge tapers continuously to the closed end of the body and stands with its end oriented towards the open end of the body perpendicularly on the capsule body. The height of the edge thus formed is such that, in the closed position of the capsule, the edge does not project beyond the cap, thus providing a flat transition from the cap to the body.

The thickness of the walls of the cap and the body can vary over the entire area. Thus, the wall thickness is generally greater in the rounded areas of the cap or the body, or at that point in the body where the bulge is formed, than in the areas where the walls run straight. In one embodiment, the walls of the cap and the body have a thickness of 0.1 to 0.5 mm.

In one possible embodiment, knobs are formed on the outside of the capsule, and in another embodiment there are three or more ribs, which run parallel to the longitudinal axis of the capsule. The advantage of these devices is that the capsule can be removed from a capsule holder e.g. as used in the aforementioned powder inhalers, in such a way that it does not get damaged or break open. The ribs or the knobs can run around the entire outside of the capsule or may only cover a part thereof. Alternatively, they may only be provided on the cap or only in the area of the body which is visible from outside in its closed state. The ribs run parallel to the longitudinal axis of the capsule and ensure that the capsule is fixed vertically in the aforementioned capsule holder. In the case of the capsule having a circular cross-section, the ribs are preferably arranged so that the cross-section of the capsule does not have rotational symmetry about its central axis. In such an embodiment, the ribs may be provided only in the area of the body which is visible when the capsule is closed. This embodiment prevents the capsule jamming in a capsule holder. In an embodiment without a bulge but with ribs on the part of the body which is visible when the capsule is closed, the ribs are designed so that the ends of the ribs which are orientated towards the open end of the body perform the function of the bulge, namely to act as a stopper for the cap, when the cap is attached to the body.

In a further embodiment, the jackets of the cap and the body describe a hollow cylinder with a round, oval, triangular, quadrilateral, hexagonal, octagonal or polygonal cross-section, where the respective upper side is open and the underside is closed. The closed underside can be flat or convex. The angled embodiments have the advantage that they can for example be stored in a more space-saving manner than the round embodiments.

In one embodiment, the elongation of the capsule (distance from the closed end of the body to the closed end of the cap in relation to the diameter when the capsule is closed) is greater than 1, in one embodiment the elongation is 1 and in yet another embodiment the elongation is smaller than 1. The latter has the advantage that the body has a larger opening for filling.

In one of the embodiments with an elongation of 1, the cap and the body are designed so that the closed capsule is spherical, which can be advantageous for automatic loading of a powder inhaler with the capsule from a reservoir.

In order to attain better sealing between the cap and the body when the filled capsules are closed, the joint between the cap and the body can be welded, adhesively bonded or wrapped, thus reducing the steam permeability to as little as a tenth. Alternatively, the entire cap can be covered with a protective film.

In another preferred embodiment, the gap may be sealed with a filler. Suitable fillers for filling the gap in this way are the pharmaceutically acceptable fillers, such as EUDRAGIT®. A filler of this kind can be inserted in the gap as a solution or suspension in a suitable, preferably highly volatile solvent. Suitable solvents include fluorochlorohydrocarbons such as methylene chloride or chloroform, fluorohydrocarbons, alcohols such as methanol, ethanol, propanol, isopropanol, alkanes such as propane, hexane, heptane, ketones such as acetone, esters such as ethyl acetate, ethers such as dimethylether or diethylether or other liquids known from the prior art to be suitable for solutions or suspensions, especially volatile liquids and those which do not attack the capsule material, do not interact chemically with pharmaceutical compositions or alter their bioavailability. The solution or suspension with the filler must be of a nature and concentration such that the solution or suspension delivers sufficient filler into the gap so that, after the solvent has evaporated, the filler left behind provides a tight seal and at the same time the solution or suspension should not be of a nature and concentration such that it is too viscous to penetrate into the gap or be drawn into it by capillary action.

Preferably, a solution of EUDRAGIT® and acetone is used to seal the gap.

It can be seen from the description that the capsule, according to the invention, is suitable for holding any kind of powdered pharmaceutical preparation which is suitable for inhalation. In a special application, the capsule contains cromoglycic acid, reproterol, beclomethasone, terbutaline, salbutamol, salmeterol, ketotifen, orciprenaline, fluticasone, insulin, ipratropium, dexamethasone, bambuterol, tiotropium, budesonide, fenoterol, clenbuterol, prednisolone, prednisone, prednylidene, methylprednisolone, formoterol, nedocromil, the salts or mixtures thereof or another cortisone preparation or atropine derivative suitable for inhalation purposes.

In a preferred embodiment, the capsule contains ipratropium bromide or tiotropium bromide.

DESCRIPTION OF THE DIAGRAMS

The diagrams show various embodiments of the capsule according to the invention by way of example, but only serve to illustrate the invention without restricting its scope.

FIG. 1 shows the simplest embodiment of the capsules according to the invention in lateral cross-section FIGS. 2a and 2b each show a different embodiment of the capsule with a tapering bulge on the body in lateral cross-section FIG. 3 shows an embodiment of the capsule with an angular bulge on the body in lateral cross-section FIG. 4 shows an embodiment of the capsule with a tapering bulge on the body and annular recess on the body and cap in lateral cross-section FIG. 5 shows an embodiment of the capsule with tapering bulge on the body and annular recess on the body and cap in frontal view FIG. 6 shows an embodiment of the capsule with tapering bulge on the body and point-shaped recesses or elevations on the body and cap in frontal view FIG. 7 shows an embodiment of the capsule with tapering bulge on the body and point-shaped elevations on the body and point-shaped holes in the cap in frontal view FIG. 8 shows an embodiment of the capsule with ribs on the body in frontal view FIG. 9 shows the capsule of FIG. 8 in horizontal cross-section FIGS. 10a, 10b and 10c show embodiments of the capsule, each with a different cross-section.

An embodiment illustrating a spherical capsule is not shown.

In FIG. 1, the simplest embodiment of the capsule according to the invention 1 is shown in cross-section. The capsule 1 consists of the cap 2 and the body 3, which are fitted telescopically one into the other. The cap 2 and the body 3 are of the same shape and each has a convex underside 4.

FIG. 2a shows a cross-section of an embodiment where a bulge 5 is formed on the body 3 of the capsule 1, this bulge tapering towards the closed end of the body. The bulge 5 stands practically vertically on the body with its side orientated towards the open end of the body. The edge thus formed demarcates the area of the body over which the cap 2 can be pushed telescopically.

Another embodiment is shown in FIG. 2b. The cross-section shows that this embodiment differs from that shown in FIG. 2a in that the wall thickness of the cap 2 or the body 3 is not uniformly great over the entire area, but rather varies over individual partial areas. In addition, the convex undersides 4 of the cap or the body each have a concave indentation at the vertex.

In FIG. 3 an embodiment is represented where the bulge 5 sits on the body almost at right angles to the upper side of the body and also the underside of the body. The embodiment of FIG. 4 represents a further development of the embodiment of FIG. 2a, where an annular recess 6 or 7 is formed in cap 2 or body 3 in order to close the capsule 1 more satisfactorily.

Figure 7:
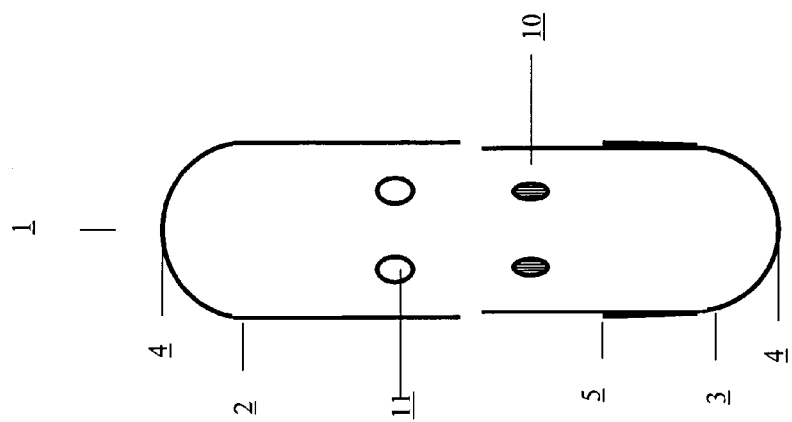
Figure 6:
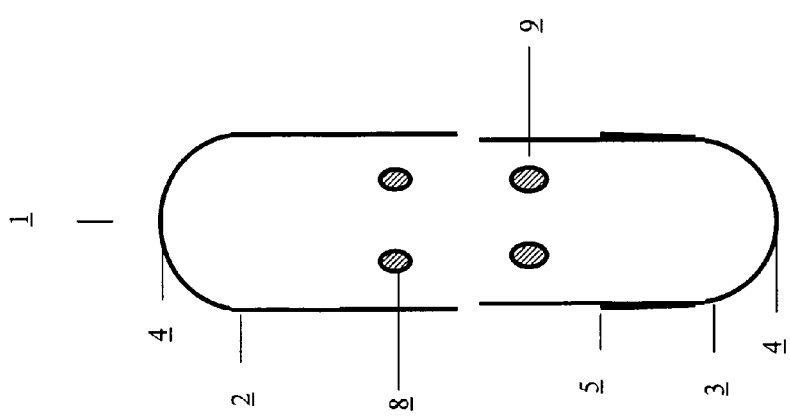
FIG. 6 shows a further variant of the invention with point-shaped recesses 8 and 9 in front view.

In FIG. 7, a variant of the capsule 1 is shown where elevations 10 are provided on the body 3 near the open end, and holes 11 are provided in the cap 2 near the open end so that the elevations 10 engage with the holes 11 when the capsule is closed.

Figure 2B:
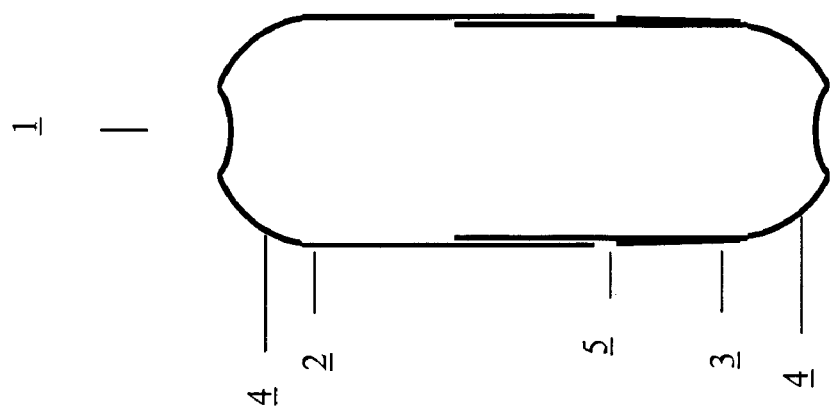
Figure 2A:
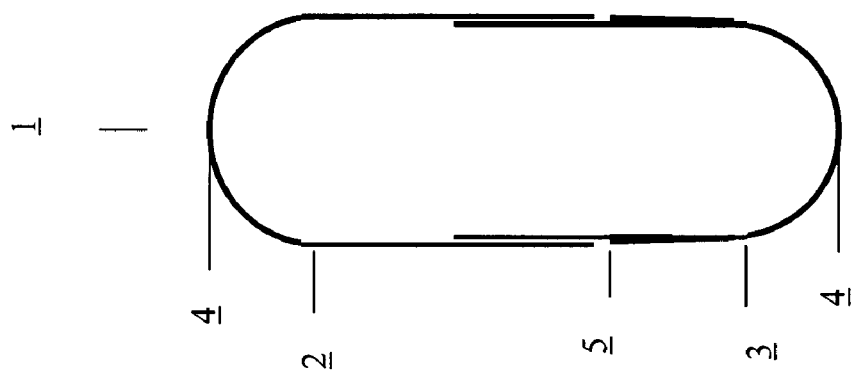
Figure 1:
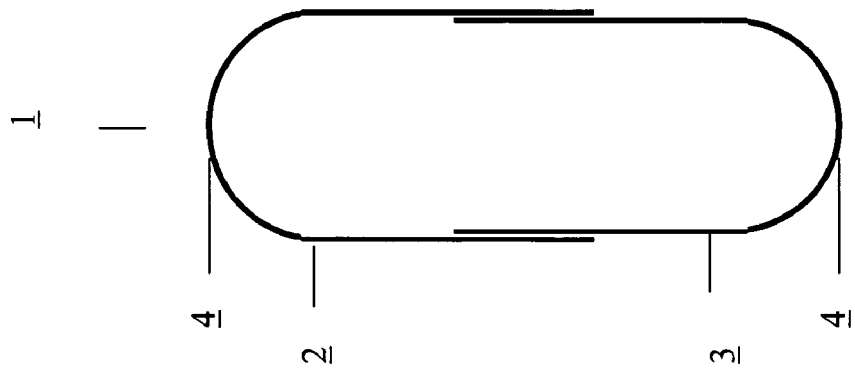
Figure 5:
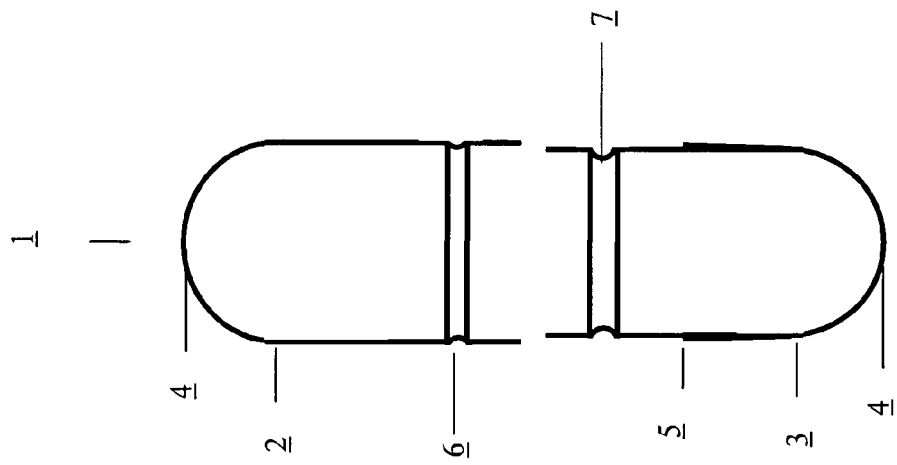
FIG. 5 shows a front view of the embodiment shown in FIG. 4 as a cross-section.
Figure 4:
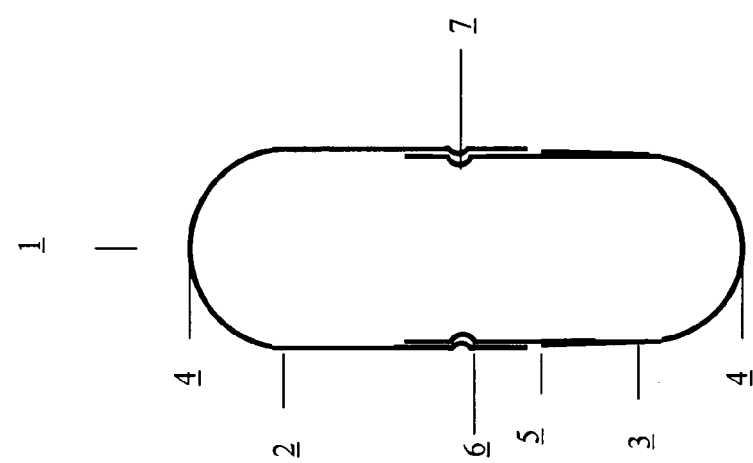
Figure 3:
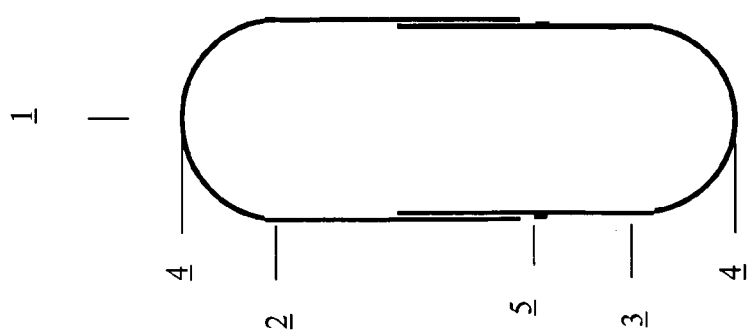
Figure 8:
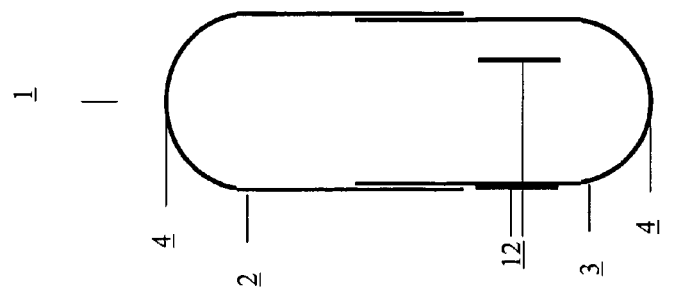

FIG. 8 shows an embodiment of the capsule 1 from outside, where ribs 12 are provided on the body 3.

Figure 10C:
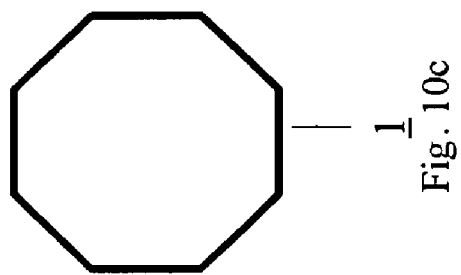
Figure 10B:
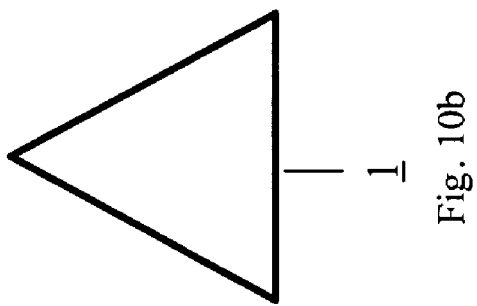
Figure 10A:
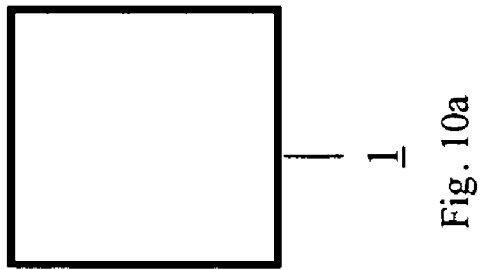
Figure 9:
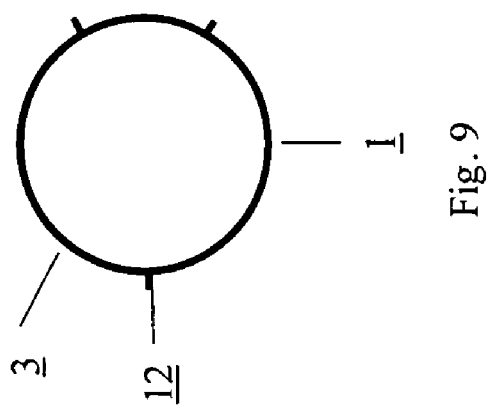

FIG. 9 shows the body 3 of the embodiment in FIG. 8 in cross-section. The cross-section shows that the three ribs 12 are not arranged with rotational symmetry about the central axis of the body. FIGS. 10a, 10b, and 10c show a capsule 1 of quadrilateral, triangular, and octagonal cross-section, respectively.

What is claimed is:
1. A capsule, comprising:
a capsule body;
a capsule cap, where the capsule body and the capsule cap are attached together telescopically so that the capsule cap is attached solidly to the capsule body in order to define and enclose a volume; and a dry, powdered pharmaceutical medicament that is suitable for inhalation by a human patient disposed within the volume defined by the capsule body and the capsule cap, wherein the capsule body and the capsule cap are formed of solid polyethylene in which does not have any holes or pores, having a Shore hardness D in the range from 65 to 73, and having a steam permeability of less than $1.3 \times 10^{-14}$ kg/(m² s Pa), and wherein the capsule body and the capsule cap are both in the shape of a cylinder of round cross-section, where an elongation of the capsule is greater than one.

2. The capsule according to claim 1, wherein walls of the capsule cap and the capsule body are 0.1 mm to 0.5 mm thick.

3. The capsule according to claim 1, wherein the capsule can withstand a force acting upon its longitudinal axis and its transverse axis of up to 15 N.

4. The capsule according to claim 1, wherein the wall of the capsule has a steam permeability of $1.5 \times 10^{-16}$ to $2 \times 10^{-16}$ kg/(m² s Pa).

5. The capsule according to claim 1, wherein one or more elevations or recesses are located on an inner surface of the capsule cap and one or more recesses or elevations are located on an outer surface of the capsule body, the elevations or recesses being arranged so that the elevations engage with the recesses when the capsule cap is attached to the capsule body.

6. The capsule according to claim 1, wherein a bulge runs in an annular shape around an outside surface of the capsule body perpendicular to a connecting axis of the capsule cap and the capsule body, a side of the bulge which is orientated towards an open end of the capsule body standing practically at right angles to an outer wall of the capsule body.

7. The capsule according to claim 1, wherein the joint or gap between the capsule body and the capsule cap is sealed by welding, adhesive bonding, wrapping or covering the capsule cap with a protective film.

8. The capsule according to claim 1, wherein the dry, powdered pharmaceutical medicament comprises one or more of: cromoglycic acid, reproterol, beclomethasone, terbutaline, salbutamol, salmeterol, ketotifen, orciprenaline, fluticasone, ipratropium, dexamethasone, bambuterol, tiotropium, budesonide, fenoterol, clenbuterol, prednisolone, prednisone, prednylidene, methylprednisolone, formoterol, nedocromil, insulin, ipratropium bromide, tiotropium bromide, a cortisone preparation, or an atropine derivative.

9. A capsule, comprising:
a capsule body
a capsule cap, where the capsule body and the capsule cap are attached together telescopically so that the capsule cap is attached solidly to the capsule body in order to define and enclose a volume; and holding the a dry, powdered pharmaceutical medicament that is suitable for inhalation by a human patient disposed within the volume defined by the capsule body and the capsule cap, wherein the capsule body and the capsule cap are formed of solid polyethylene in which does not have any holes or pores, having a Shore hardness D in the range from 65 to 73, and having a steam permeability of less than $1.3 \times 10^{-14}$ kg/(m² s Pa), wherein the capsule body and the capsule cap are both in the shape of a cylinder of round cross-section, where an elongation of the capsule is greater than one, and wherein a joint between the capsule body and the capsule cap is sealed by filling with a pharmaceutically acceptable filler.

10. The capsule according to claim 9, wherein the filler is an acryl-polymer resin.

11. The capsule according to claim 9, wherein the dry, powdered pharmaceutical medicament comprises one or more of: cromoglycic acid, reproterol, beclomethasone, terbutaline, salbutamol, salmeterol, ketotifen, orciprenaline, fluticasone, ipratropium, dexamethasone, bambuterol, tiotropium, budesonide, fenoterol, clenbuterol, prednisolone, prednisone, prednylidene, methylprednisolone, formoterol, nedocromil, insulin, ipratropium bromide, tiotropium bromide, a cortisone preparation, or an atropine derivative.

* * * * *